(12) United States Patent
Schikora

(10) Patent No.: US 7,179,278 B2
(45) Date of Patent: Feb. 20, 2007

(54) DEVICE FOR PERFORMING ACUPUNCTURE USING LASER RADIATION

(75) Inventor: Detlef Schikora, Wehrden (DE)

(73) Assignee: LASERneedle Entwicklungsgesellschaft GmbH, Beverungen (DE)

( * ) Notice: Subject to any disclaimer, the term of this patent is extended or adjusted under 35 U.S.C. 154(b) by 761 days.

(21) Appl. No.: 10/432,118

(22) PCT Filed: Jul. 24, 2001

(86) PCT No.: PCT/EP01/08504

§ 371 (c)(1),
(2), (4) Date: May 19, 2003

(87) PCT Pub. No.: WO02/40098

PCT Pub. Date: May 23, 2002

(65) Prior Publication Data

US 2004/0092859 A1    May 13, 2004

(30) Foreign Application Priority Data

Nov. 20, 2000   (DE) .......................... 200 19 703 U

(51) Int. Cl.
*A61N 5/067* (2006.01)

(52) U.S. Cl. .............. 607/89; 607/88; 606/2; 606/10; 606/13

(58) Field of Classification Search .............. 606/2–13; 607/88–89
See application file for complete search history.

(56) References Cited

U.S. PATENT DOCUMENTS

| | | | | |
|---|---|---|---|---|
| 4,553,546 A | * | 11/1985 | Javelle | 607/89 |
| 4,729,621 A | * | 3/1988 | Edelman | 385/33 |
| 5,172,685 A | * | 12/1992 | Nudelman | 600/108 |
| 5,188,632 A | * | 2/1993 | Goldenberg | 606/7 |
| 5,190,535 A | * | 3/1993 | Daikuzono | 606/13 |
| 5,250,068 A | | 10/1993 | Ideguchi et al. | 606/189 |
| 5,334,190 A | * | 8/1994 | Seiler | 606/5 |
| 5,807,383 A | * | 9/1998 | Kolesa et al. | 606/7 |
| 6,074,411 A | * | 6/2000 | Lai et al. | 607/89 |
| 6,306,160 B1 | | 10/2001 | Nidetzky | 607/89 |
| 6,450,170 B1 | * | 9/2002 | Friedman | 128/898 |

FOREIGN PATENT DOCUMENTS

| | | |
|---|---|---|
| DE | 27 40 969 | 3/1979 |
| DE | 37 29 288 A1 | 3/1989 |
| DE | 196 07 174 A1 | 8/1997 |
| DE | 197 37 675 A1 | 3/1999 |
| EP | 0 416 150 B1 | 3/1991 |
| EP | 0 437 636 A1 | 7/1991 |
| EP | 0 495 757 A1 | 7/1992 |
| EP | 0 722 750 B1 | 7/1996 |

* cited by examiner

Primary Examiner—Henry M Johnson, III
(74) Attorney, Agent, or Firm—Davis & Bujold, P.L.L.C.

(57) ABSTRACT

A device for performing acupuncture on a patient using laser radiation as a device for producing laser radiation and a handpiece (1) which is connected thereto and which is brought into contact with the body of the patient in order to apply the laser radiation. The handpiece (1) has at least one light conducting fiber (4) which is connected to the device (7) for producing laser radiation and which is in contact with the body of the patient during the acupuncture and applies the laser radiation thereto.

20 Claims, 4 Drawing Sheets

DEVICE FOR PERFORMING ACUPUNCTURE USING LASER RADIATION

FIELD OF THE INVENTION

The invention relates to an apparatus for performing acupuncture on a patient by means of laser radiation, having a device for generating the laser radiation and having a handpiece which is connected thereto and is intended to come into contact with the body of the patient in order to apply the laser radiation.

BACKGROUND OF THE INVENTION

Apparatus of the generic type for performing acupuncture by means of laser radiation are known, for example, from EP 0 722 750 B1, EP 0 416 150 B1, DE 197 37 675 A1 or DE 89 11 606 U1. In these apparatus, semiconductor laser diodes with a relatively low output power for a wavelength range from 630 to 950 nm are often used to generate the laser radiation. To achieve a compact structure of the apparatus, the devices for generating the laser radiation are generally accommodated in the handpiece. The laser radiation is then focussed at the outlet opening of the handpiece with the aid of optics.

However, a drawback of these apparatus is that the laser radiation which they emit has such a low intensity that all the energy is absorbed in just the upper layers of the skin of the treated patient and is distributed over the area of the collagen fibers. As a result, it is impossible to exert sufficient stimulation at the location which is to be treated by acupuncture, which is necessary in order to achieve a treatment result which is comparable to that obtained with treatment using standard acupuncture needles.

Therefore, the apparatus described, although they can be used in dermatology to heal wounds and scars, cannot be used to stimulate acupuncture points.

With acupuncture using standard metal needles, which has long been known even throughout Europe, drawbacks are firstly the sterility problems which may occur during treatment and secondly the fact that the tissue is traumatized in the region of the acupuncture points. Furthermore, metal needles of this type cannot be used for patients with a fear of needles and in particular for children.

Therefore, it is an object of the present invention to provide an apparatus for performing acupuncture on a patient by means of laser radiation which is able to produce a sufficient stimulating action even in the relatively deep-lying skin layers which have to be reached for an acupuncture treatment to be successful.

SUMMARY OF THE INVENTION

According to the invention, this object is achieved through the fact that the handpiece has at least one optical fiber, which is connected to the device for generating the laser radiation and which, during the acupuncture, is in contact with the patient's body and applies the laser radiation to it.

On account of the optical fiber, which is in contact with the patient's body and is arranged inside the handpiece, the full intensity of the electromagnetic energy which is emitted by the device for generating the laser radiation can penetrate into the patient's body and produce stimulation with a high energy density which does not, however, injure the tissue.

Therefore, an acupuncture treatment can be carried out extremely gently yet its therapeutic action is at least equivalent to treatment with standard metal needles. Moreover, the range of patients who can be treated can advantageously be extended to encompass people who were not previously able to be treated using standard metal needles. Therefore, the apparatus according to the invention can be used without problems in all medical institutions and also by non-medical practitioners, since the stimulating action is sufficient but is also physiologically harmless.

In a particularly advantageous refinement of the invention, it is possible to provide that the cross section of the at least one optical fiber is larger in the region of the device for generating the laser radiation than in the region which is in contact with the patient's body during acupuncture.

This reduction in the cross section advantageously increases the energy density of the laser beams which causes the stimulating action on the surface of the body, for the same output power from the laser. This opens up an even wider range of applications for the apparatus according to the invention and means that, depending on the cross section of the optical fiber, it is possible to penetrate into skin layers at different depths.

In particular the power saving in the device for generating the laser radiation is a notable advantage in this context, since in this way it is possible to use relatively inexpensive lasers and consequently the costs of the apparatus as a whole remain acceptable.

In a further configuration of the invention, it is possible to provide for there to be a plurality of handpieces which each have one optical fiber.

In this way, it is possible, as is inherently required in conventional acupuncture, for a plurality of locations on the patient's body to be treated simultaneously, so that energy blockages at various points in the meridian system can be eliminated. Compared to the laser acupuncture appliances described in the introduction, this constitutes a significant advantage, since simultaneous treatment of a plurality of acupuncture locations was not provided for and was indeed impossible.

There are then various options for connecting the individual optical fibers accommodated in the individual handpieces to the device for generating the laser radiation.

Firstly, the device for generating the laser radiation may have a plurality of independent laser beam generation means, each individual optical fiber being connected to in each case one laser beam generation means. This embodiment, which is presented in the manner of an array, is designed according to the principle that each laser beam generation means supplies precisely one optical fiber, so that after the array has been started up the individual acupuncture points can be stimulated and the stimulating action on all the selected acupuncture points takes place simultaneously.

Alternatively, the device for generating the laser radiation may have at least two laser beam generation means which are connected to one another by means of one optical fiber coupling element, each individual optical fiber being connected to the fiber coupling element.

In this case, the individual optical fibers are supplied by the optical fiber coupling element, making it possible for each individual optical fiber to be supplied with polychromatic laser radiation, i.e. with laser radiation of at least two different wavelengths, so that the absorption of the laser radiation can take place in at least two different tissue depths. Of course, in this embodiment it is also possible for each individual optical fiber to be supplied with monochromatic laser radiation.

Finally, there is also the option of the device for generating the laser radiation having a laser beam generation means which is connected to each of the individual optical fibers via a fiber bundle. In this embodiment, it is possible to utilize the flexibility which is inherent to a fiber bundle of this nature in order thereby to make the individual handpieces relatively simple to handle.

The optical fiber is protected if, in a further configuration of the invention, the handpiece has a housing for holding the optical fiber. In this context, simple yet at the same time very secure application of the handpiece to the patient's body is ensured by a securing element for applying the handpiece to the patient's body being arranged at the outer periphery of the housing.

Further advantageous configurations and refinements of the invention will emerge from the remaining subclaims and from the exemplary embodiment which is outlined below with reference to the drawing, in which;

DETAILED DESCRIPTION OF THE INVENTION

Figure 1:
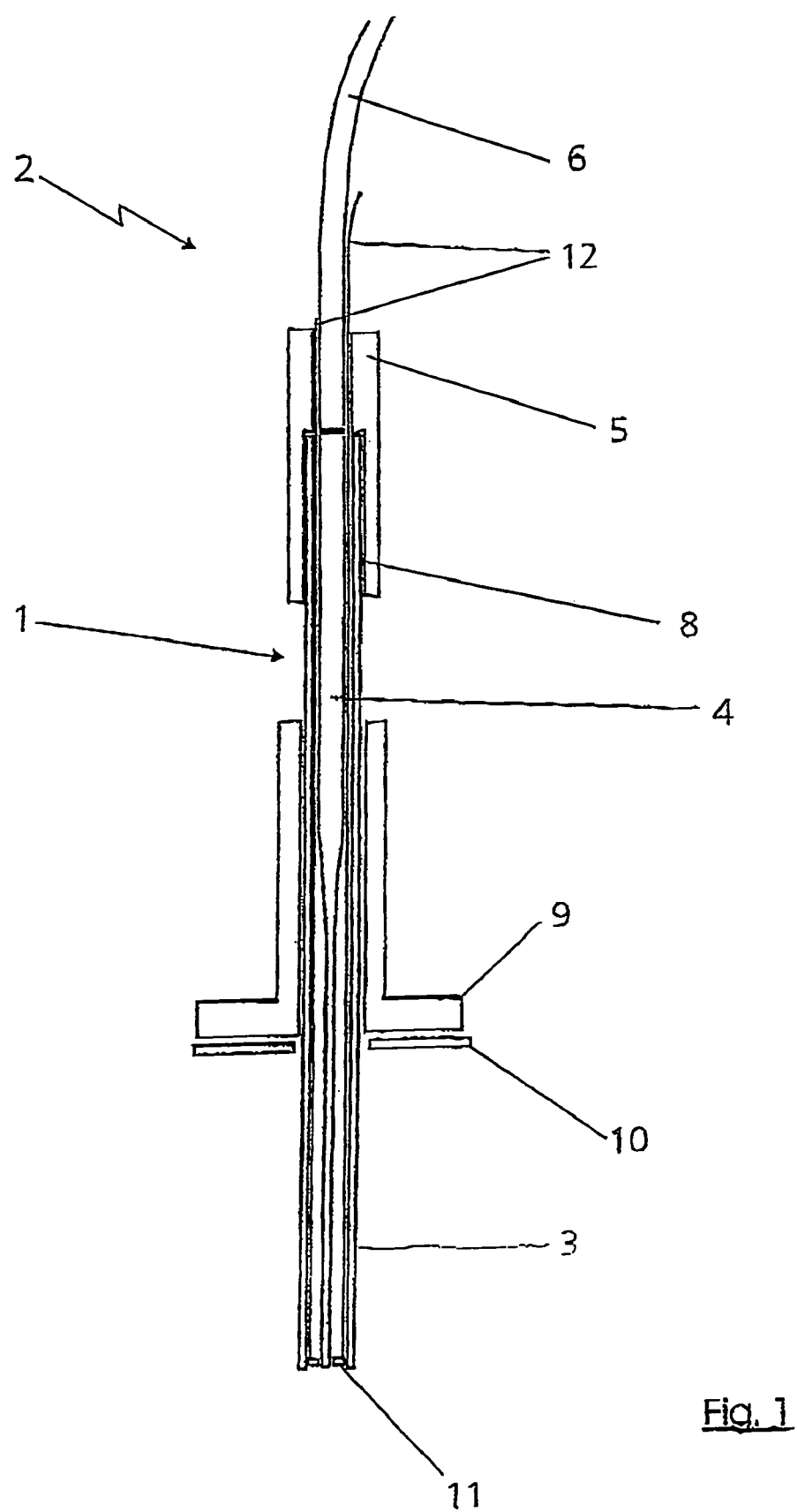
FIG. 1 shows a section through a handpiece of the acupuncture apparatus according to the invention.

FIG. 1 shows a handpiece as part of an apparatus 2 for performing acupuncture on a patient (not shown) by means of laser radiation. The structure of the apparatus 2 as a whole can be seen from FIGS. 2, 3 and 4 and is described in more detail with reference to these figures.

Figure 2:
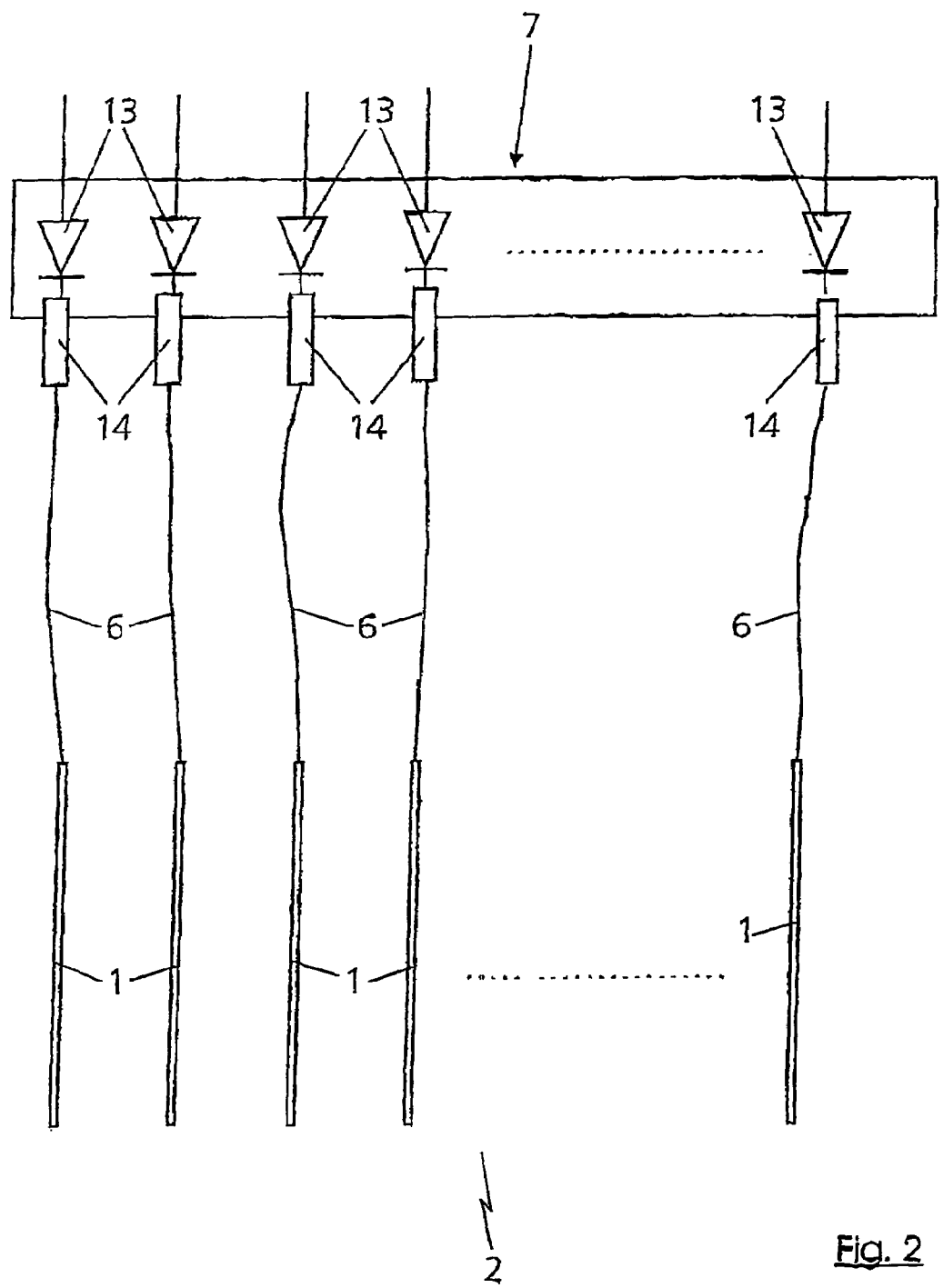
FIG. 2 shows a first embodiment of the acupuncture apparatus according to the invention with a plurality of handpieces.
Figure 3:
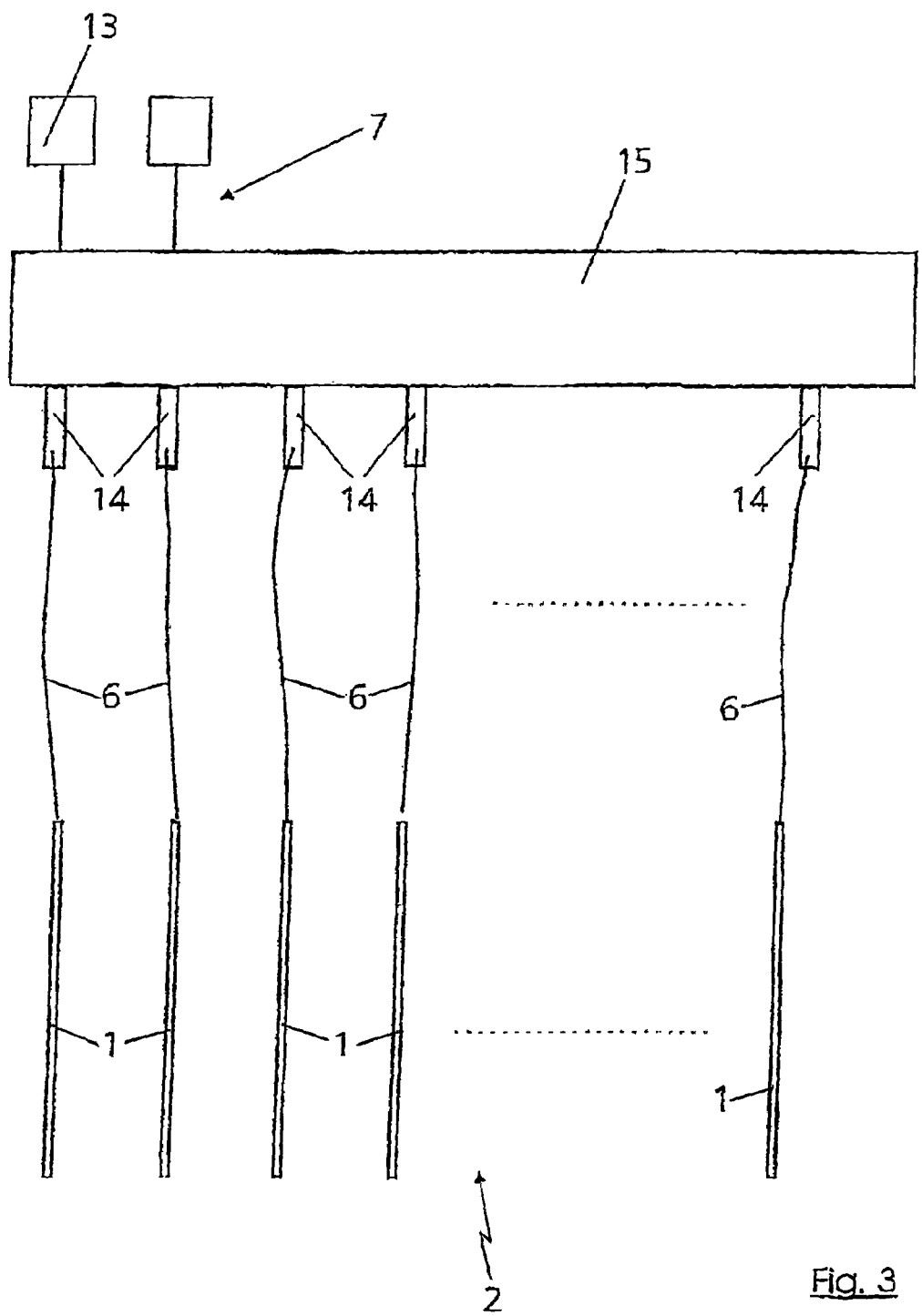
FIG. 3 shows a second embodiment of the acupuncture apparatus according to the invention with a plurality of handpieces.
Figure 4:
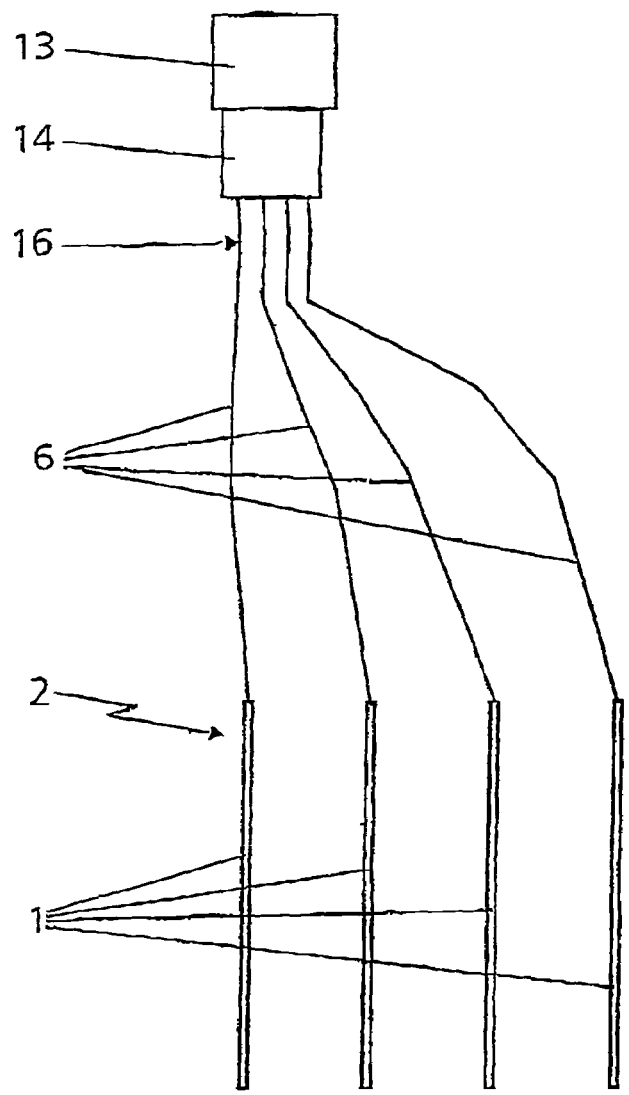
FIG. 4 shows a third embodiment of the acupuncture apparatus according to the invention with a plurality of handpieces.

The handpiece 1 has a sleeve-like, cylindrical housing 3, in the interior of which an optical fiber 4 is accommodated. A connecting optical fiber 6, which connects the optical fiber 4 to a device 7 for generating laser radiation, which is only illustrated in FIGS. 2, 3 and 4, is fitted to the optical fiber 4 via an optical coupling element 5. The laser radiation which is generated by the device 7 can therefore pass via the connecting optical fiber 6 into the optical fiber 4 and, when the handpiece 1 has been placed onto the body of the patient, can penetrate into the skin layers of the patient. In the present case, to securely connect the optical fiber 4 to the connecting optical fiber 6, the optical coupling element 5 is provided with a screw thread 8 for fitting it to the housing 3. Of course, other connection options are also conceivable for this purpose.

To apply or attach the handpiece 1 to the patient's body, there is a securing element 9, which can be mechanically connected to the housing 3, at the outer periphery of the housing 3. In the present case, this mechanical connection is created by the securing element 9 consisting of rubber, for example of silicone, so that there is a relatively high friction with respect to the housing 3, which consists of a ceramic, preferably a corundum ceramic. Of course, the housing 3 may also consist of a light metal, preferably of titanium, in order to have the minimum possible mass while nevertheless achieving a high strength on the part of the housing 3.

As an alternative to the mechanical connection between the securing element 9 and the housing 3 by means of friction, it is also possible for a clamp (not shown) to be fitted, for example, to the outer periphery of the securing element 9, pressing the securing element 9 firmly onto the housing 3. On that side of the securing element 9 which faces the patient's body, there is a dermatologically tolerated, double-acting adhesive ring 10 which is intended to be applied to the patient's body.

Therefore, if the handpiece 1 is to be attached to the patient's body, the securing element 3 is moved along the housing 3 toward the patient's body until the adhesive ring 10 comes into contact with the patient's body and sticks to it. As a result of the mechanical connection between the securing element 9 and the housing 3, the handpiece 1 can then no longer slip and remains in contact with the patient's body until the securing element 9 is released by the person carrying out the treatment.

Furthermore, there are two electrodes 11 inside the housing 3, which are intended to measure the skin resistance of the patient's body. With this measurement of the skin resistance which is known per se, it is possible to determine or select the points which are required to undergo acupuncture. The two electrodes 11 are each provided with connecting lines 12, the function of which will be explained in more detail at a later time.

It can also be seen from FIG. 1 that the cross section of the optical fiber 4 in the region of the optical coupling element 5 is larger than in the region which is in contact with the patient's body when acupuncture is being performed. In this way, the energy density of the laser radiation which is introduced into the optical fiber 4 via the connecting optical fiber 6 is increased in inverse proportion to the ratio of the cross section at the outlet point to the cross section at the inlet point of the laser radiation. This higher energy density also enables relatively deep-lying acupuncture points of the patient to be reached by the laser radiation, which is imperative for various types of acupuncture treatment.

In the present case, the reduction in the cross-sectional area of the optical fiber 4 is ⅓ to ¹⁄₁₀, an optically active area with an extent of approx. 0.05–0.1 mm being formed at the tip of the optical fiber 4. By using different changes in the cross section of the optical fiber 4 and as a result of the change in the energy density which this brings about, the laser radiation reaches different penetration depths, as is achieved in a similar way with metal needles for conventional acupuncture which are of different lengths.

In an embodiment which is not shown, it is also possible to dispense with the connecting optical fiber 6, which means that the optical fiber 4 is then directly connected to the device 7 for generating the laser radiation. In principle, the reduction in the cross section of the optical fiber 4 can be distributed over its entire length.

The optical fiber 4 has a coaxial structure with a core (not shown) and a sheath (likewise not shown). In this case, the core of the optical fiber 4 may consist of quartz glass or of plastic, depending on the wavelength of the laser radiation which is to be transmitted.

In this case, the core and the sheath of the optical fiber 4, as is known, are constructed in such a way that total reflection of the laser radiation occurs at the sheath and the light wave cannot leave the core of the optical fiber 4. Of course, this must be the case even if the cross section of the optical fiber 4 narrows.

The wavelength ranges of the laser radiation used may vary from the near ultraviolet to the near infrared, so that wavelengths of approx. 350–980 nm can be used. In this context, it has emerged that wavelengths in a range from approx. 800–950 nm are particularly suitable for penetrating into relatively deep-lying skin regions. Therefore, by varying the wavelength of the laser radiation used, it is possible to adapt to the different regions of the body and the different therapeutic objectives of the acupuncture treatment, since different wavelengths also lead to different laser radiation penetration depths.

FIG. 2 shows a new type of embodiment of the device 2 as a whole, which is provided with a plurality of handpieces 1. There will in general be four to ten handpieces 1, depending on the type of acupuncture treatment. In this way, it is possible for a plurality of points on the patient's body to be subjected to acupuncture simultaneously, as is the case with conventional acupuncture using metal needles.

In this case, the device 1 has a number of laser beam generation means 13 which matches the number of handpieces 1 and therefore of optical fibers 4, these laser beam generation means 13 operating independently of one another and each being individually connected to the optical fibers 4. Suitable laser beam generation means 13 are in principle laser diodes, such as for example gallium arsenide laser diodes or gallium nitride laser diodes, which are in this case arranged in the form of an array. As an alternative, it is possible to use different or identical laser beam generation means 13 to generate laser radiation of suitable wavelengths, so that the individual handpieces 1 may if appropriate also bring about different penetration depths into the patient's body.

Each individual laser beam generation means 13 is assigned collimator and focussing optics 14, from which the individual connecting optical fibers 6 start, ultimately, as described above, leading to the individual optical fibers 4. Therefore, the device 7 for generating the laser radiation is arranged outside the handpiece 1, with the result that relatively powerful laser beam generation means 13 can be used, since they do not have to be matched to the relatively small size of the individual handpieces 1. However, on account of the reduction in the cross section of the individual optical fibers 4 described above, such powerful laser beam generation means 13 are not necessarily required.

As has already been mentioned above, as an alternative to the optical fibers 4 being connected to the corresponding collimator and focussing optics 14 via the connecting optical fiber 6, it is also possible for the optical fibers 4 to be connected directly to the associated collimator and focussing optics 14.

In the embodiment of the apparatus 2 shown in FIG. 3, the device 7 for generating the laser radiation has two laser beam generation means 13 which are independent of one another and may, for example, be designed as gas discharge lasers or as solid-state lasers. Of course, it is also possible to use the laser diodes which have already been described above, and it is also possible to use a different number of laser beam generation means 13. The two laser beam generation means 13 are connected to one another via an optical fiber coupling element 15, the operation of which is known per se. Once again, the collimator and focussing optics 14 described above are in each case arranged at the output of the fiber coupling element 15. From the collimator and focussing optics 14, as in the embodiment shown in FIG. 2, the connecting optical fibers 6 in each case lead to the individual handpieces 1 with the optical fibers 4.

In this device 2, the individual laser beams of the two laser beam generation means 13 can be transmitted via the optical fiber coupling element 15 to the optical fibers 4 in any desired way; they may also be mixed as desired. In this way, it is possible for laser radiation of any desired wavelength to be introduced into the patient's body, both in the form of monochromatic laser radiation and in the form of polychromatic laser radiation.

In the apparatus shown in FIG. 4, the device 7 for generating the laser radiation has a laser beam generation means 13 which may once again be designed as a laser diode, as a gas discharge laser or as a solid-state laser and which is connected, via a single set of collimator and focussing optics 14 and via fiber bundle 16, to each of the individual optical fibers 4 of the individual handpieces 1. Therefore, the same laser radiation is applied to all the optical fibers 4. The fiber bundle 16 results in a flexibility which makes the individual handpieces 1 simple to handle.

Figure 5:
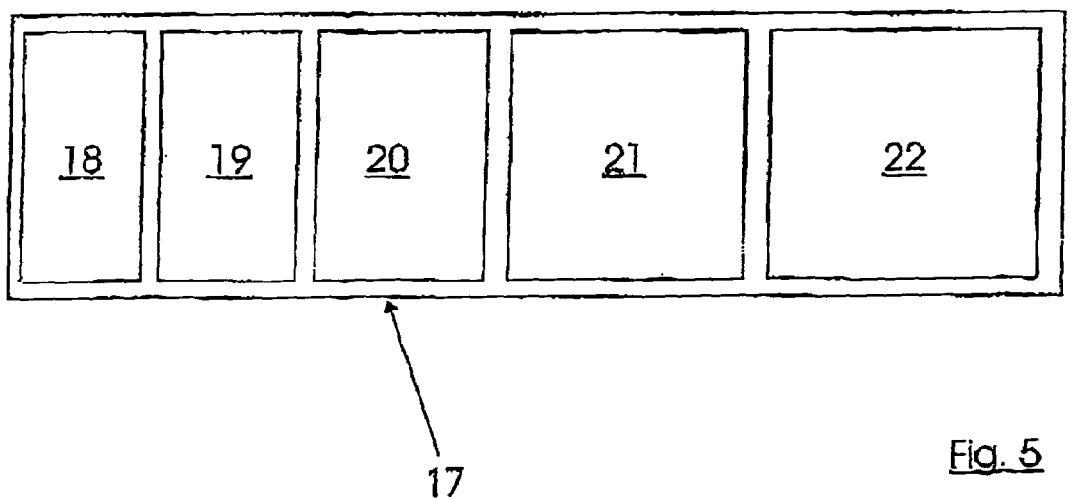
FIG. 5 diagrammatically depicts a control unit for the apparatus according to the invention.

FIG. 5 shows a control unit 17 which is used to control the devices 7 for generating the laser radiation and for further functions which are to be described in more detail below. For this purpose, the control unit 17 has a supply module 18, which converts the mains voltage into a DC voltage of 2–8 volts which may be required for operation of the device 7.

Furthermore, there is a module 19 which is used to measure the intensity of the laser radiation before its application and therefore to match it to the different stimulation thresholds of the individual patients. The module 19 can therefore be described as a photometer.

A further module 20 is used for the time control of the laser radiation and switches on the respective laser generation means 13. In this way, the duration of the acupuncture treatment can be set and controlled.

A further module 21 of the control device 17 is used to modulate the intensity of the laser radiation from the laser beam generation means 13 with physiologically relevant Bahr or Nogier frequencies.

Finally, there is also a module 22 for holding the device 7 for generating the laser radiation, which in the individual embodiments shown in FIGS. 2, 3 and 4 respectively holds either the laser diode array comprising the laser beam generation means 13, the optical fiber coupling element 15 or if appropriate also the fiber bundle 16.

Furthermore, the connecting lines 12 which lead from the electrodes 11 can be connected to the control unit 17, in order to generate a signal when an acupuncture point has been found.

The invention claimed is:

1. An apparatus for performing acupuncture on a patient by way of laser radiation, the apparatus having a device for generating the laser radiation and having a handpiece which is connected thereto and is intended to come into contact with a body of the patient to apply the laser radiation thereto, in which apparatus the handpiece (1) has at least one optical fiber (4) which is connected to the device (7) for generating the laser radiation and which has a coaxial structure with a core and a sheath and, during the acupuncture, is in contact with the body of the patient and applies the laser radiation to the body;

wherein a cross section of the core of the at least one optical fiber (4) is larger in a region of the device (7) for generating the laser radiation than in the region which is in contact with the patient's body during acupuncture.

2. The apparatus according to claim 1, wherein at least one optical fiber (4) is connected to the device (7) for generating the laser radiation via collimator and focusing optics (14).

3. The apparatus according to claim 2, wherein at least one optical fiber (4) is directly connected to the collimator and focusing optics (14).

4. The apparatus according to claim 2, wherein at least one optical fiber (4) is connected to the collimator and focusing optics (14) via a connecting optical fiber (6).

5. The apparatus according to claim 4, wherein at least one optical fiber (4) runs exclusively inside the handpiece (1) and is connected to the connecting optical fiber (6) by an optical coupling element (5).

6. The apparatus according to claim 1, wherein the apparatus includes a plurality of handpieces (1) which each having an optical fiber (4).

7. The apparatus according to claim 6, wherein a securing element (9) for attaching the handpiece (1) to the patient's body is arranged at an outer periphery of the housing (3).

8. The apparatus according to claim 7, wherein the securing element (9) comprises rubber.

9. The apparatus according to claim 7, wherein an adhesive ring (10) for attachment to the body of the patient is arranged on a side of the securing element (9) which faces the body of the patient.

10. The apparatus according to claim 7, wherein a securing element (9) is mechanically connected to the housing (3).

11. The apparatus according to claim 1, wherein the device (7) for generating the laser radiation is arranged outside the handpiece (1).

12. The apparatus according to claim 10, wherein the mechanical connection between a securing element (9) and the housing (3) takes place by friction.

13. The apparatus according to claim 1, wherein the device (7) for generating the laser radiation has a plurality of independent laser beam generating means (13) and, in each case, each of the at least one optical fiber (4) is connected to one of the plurality of independent laser beam generating means (13).

14. The apparatus according to claim 1, wherein the device (7) for generating the laser radiation has at least two laser beam generating means (13) which are connected to one another by a fiber coupling element (15), and each of the at least one optical fiber (4) is connected to the fiber coupling element (15).

15. The apparatus according to claim 1, wherein the core of the optical fiber (4) comprises quartz glass.

16. The apparatus according to claim 1, wherein the core of the optical fiber (4) comprises plastic.

17. The apparatus according to claim 1, wherein the handpiece (1) has a housing (3) for holding the optical fiber (4).

18. The apparatus according to claim 1, wherein a control unit (17) for controlling one of the handpiece (1) and the device (7) for generating the laser radiation, has a supply module (18), a module (19) for measuring the intensity of the laser radiation, a module (20) for time control of the laser radiation, a module (21) for modulating the intensity of the laser radiation and a module (22) for holding the device (7) for generating the laser radiation.

19. The apparatus according to claim 1, wherein at least one electrode (11), for measuring a skin resistance of the body of the patient, is arranged inside the handpiece (1).

20. The apparatus according to claim 19, wherein at least one electrode (11) has an electrical connecting line (12) to the control unit (17).

* * * * *